(12) United States Patent
Richelsoph

(10) Patent No.: US 7,105,024 B2
(45) Date of Patent: Sep. 12, 2006

(54) ARTIFICIAL INTERVERTEBRAL DISC

(75) Inventor: Marc Richelsoph, Bartlett, TN (US)

(73) Assignee: Aesculap II, Inc., Center Valley, PA (US)

( * ) Notice: Subject to any disclaimer, the term of this patent is extended or adjusted under 35 U.S.C. 154(b) by 136 days.

(21) Appl. No.: 10/430,861

(22) Filed: May 6, 2003

(65) Prior Publication Data
US 2004/0225362 A1  Nov. 11, 2004

(51) Int. Cl.
*A61F 2/44* (2006.01)

(52) U.S. Cl. .............................. 623/17.13; 623/17.14; 623/17.15

(58) Field of Classification Search .............. 623/17.11, 623/17.12, 17.13, 17.14, 17.15, 17.16
See application file for complete search history.

(56) References Cited

U.S. PATENT DOCUMENTS

| | | | |
|---|---|---|---|
| 4,759,769 A | 7/1988 | Hedman et al. | |
| 5,258,031 A | 11/1993 | Salib | |
| 5,314,477 A | 5/1994 | Marnay | |
| 5,401,269 A | 3/1995 | Büttner-Janz et al. | |
| 5,507,816 A | 4/1996 | Bullivant | |
| 5,562,738 A | 10/1996 | Boyd et al. | |
| 5,782,832 A | 7/1998 | Larsen et al. | |
| 5,865,846 A | 2/1999 | Bran et al. | |
| 5,888,226 A | 3/1999 | Rogozinski | |
| 5,893,889 A | 4/1999 | Harrington | |
| 6,001,130 A | 12/1999 | Bryan | |
| 6,013,103 A | 1/2000 | Kaufman et al. | |
| 6,063,121 A * | 5/2000 | Xavier et al. ............. | 623/17.15 |
| 6,146,421 A * | 11/2000 | Gordon et al. ............ | 623/17.15 |
| 6,368,350 B1 * | 4/2002 | Erickson et al. ......... | 623/17.14 |
| 6,443,987 B1 | 9/2002 | Bryan | |
| 6,491,726 B1 | 12/2002 | Pappas | |
| 6,494,915 B1 | 12/2002 | Villar Gonzalez et al. | |
| 6,517,580 B1 * | 2/2003 | Ramadan et al. ......... | 623/17.15 |
| 6,520,996 B1 | 2/2003 | Manasas et al. | |
| 6,572,653 B1 | 6/2003 | Simonson | |
| 6,582,466 B1 * | 6/2003 | Gauchet ................... | 623/17.11 |
| 6,645,248 B1 * | 11/2003 | Casutt ..................... | 623/17.12 |
| 6,682,562 B1 * | 1/2004 | Viart et al. .............. | 623/17.14 |
| 6,733,532 B1 * | 5/2004 | Gauchet et al. .......... | 623/17.12 |
| 2003/0055427 A1 | 3/2003 | Graf | |
| 2003/0191534 A1 | 10/2003 | Viart et al. | |
| 2004/0002761 A1 | 1/2004 | Rogers et al. | |

FOREIGN PATENT DOCUMENTS

| | | |
|---|---|---|
| DE | 2 263 842 | 12/1972 |
| DE | G 90 00 094.3 | 1/1990 |
| EP | 0282 161 A1 | 2/1988 |
| EP | 0 560 141 | 9/1993 |
| EP | 0 747 025 | 12/1996 |

(Continued)

OTHER PUBLICATIONS

Partial European Search Report; Aug. 22, 2005; Berlin.

*Primary Examiner*—Pedro Philogene
(74) *Attorney, Agent, or Firm*—RatnerPrestia

(57) ABSTRACT

An artificial intervertebral disc includes housing members including spaced inner surfaces facing each other and oppositely facing outer surfaces for engaging spaced apart vertebral surfaces. Bearing surfaces extend from each of the inner surfaces for engaging each other while allowing for low friction and compression resistant movement of the housing members relative to each other while under compression. Load sharing pads are disposed between the inner surfaces and about at least a portion of the bearing surfaces for sharing absorption compressive loads with the bearing surfaces while limiting the relative movement of the housing members.

10 Claims, 13 Drawing Sheets

FOREIGN PATENT DOCUMENTS

| | | |
|---|---|---|
| EP | 1 103 237 A2 | 5/2001 |
| EP | 1 103 237 A3 | 4/2002 |
| EP | 1 344 508 | 9/2003 |
| FR | 2 694 882 | 2/1994 |
| FR | 2 799 638 A1 | 10/1999 |
| FR | 2 718 635 | 1/2001 |
| WO | WO 94/04100 | 3/1994 |
| WO | WO 99/05995 | 2/1999 |
| WO | WO 00/04851 | 2/2000 |
| WO | WO 00/13619 | 3/2000 |
| WO | WO 00/35385 | 6/2000 |
| WO | WO 01/01893 A1 | 1/2001 |
| WO | WO 03/094806 A1 | 11/2003 |

* cited by examiner

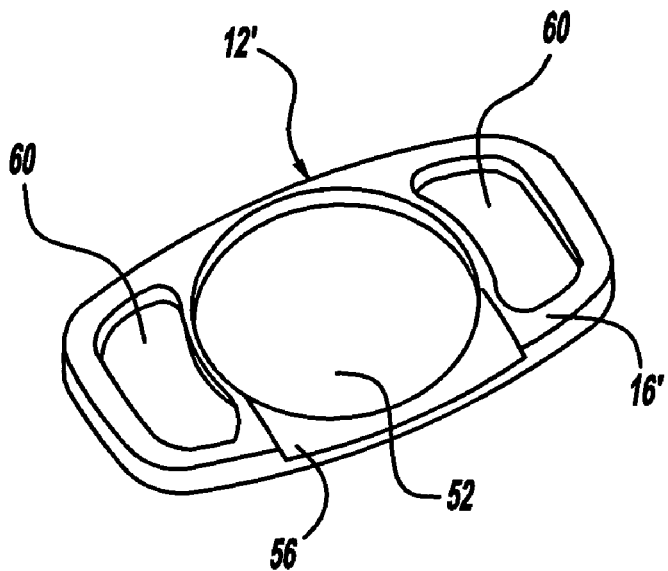
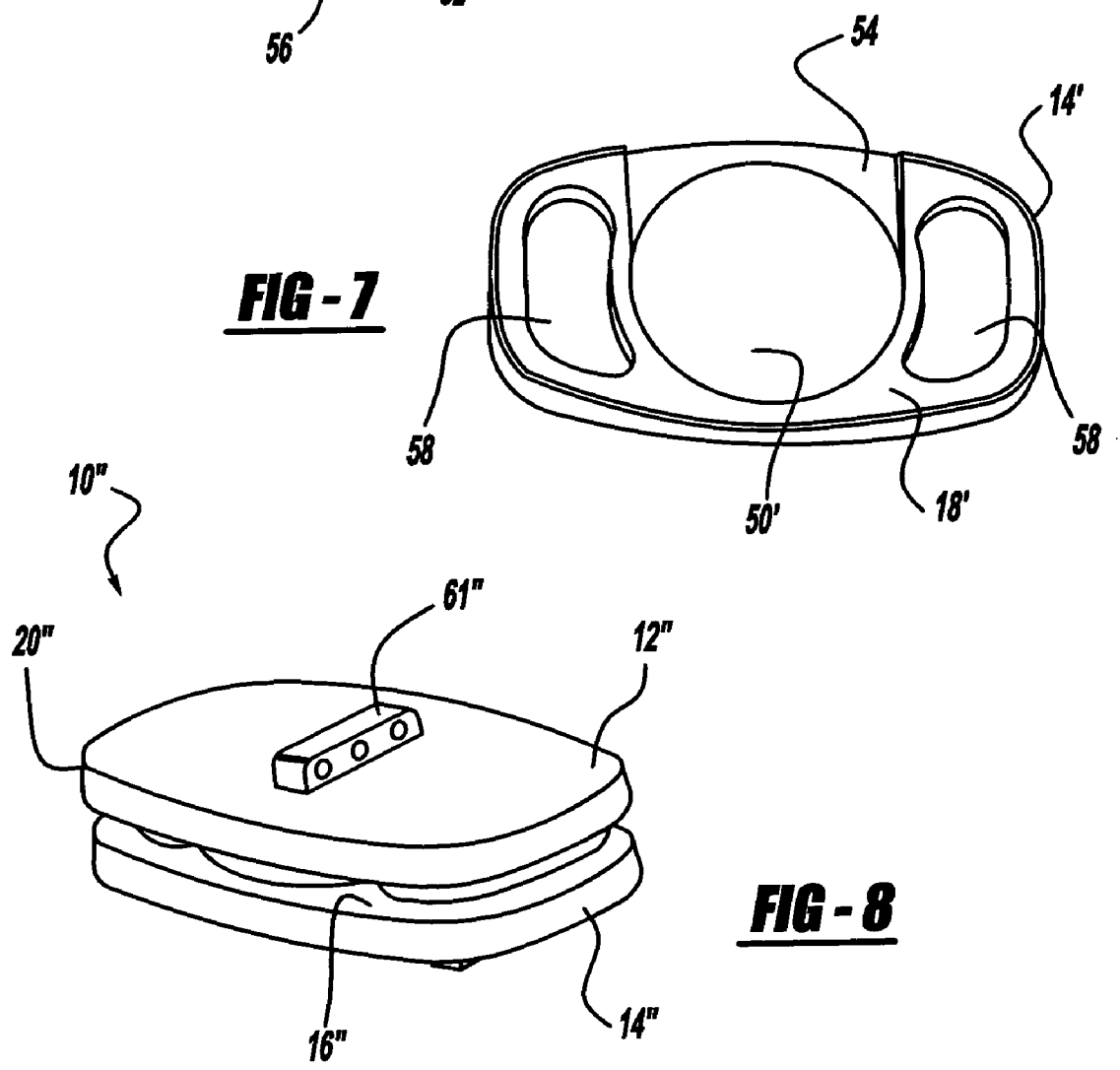
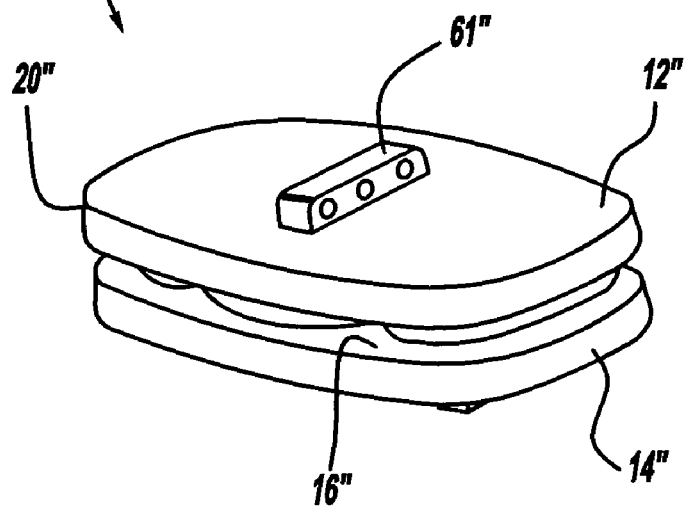

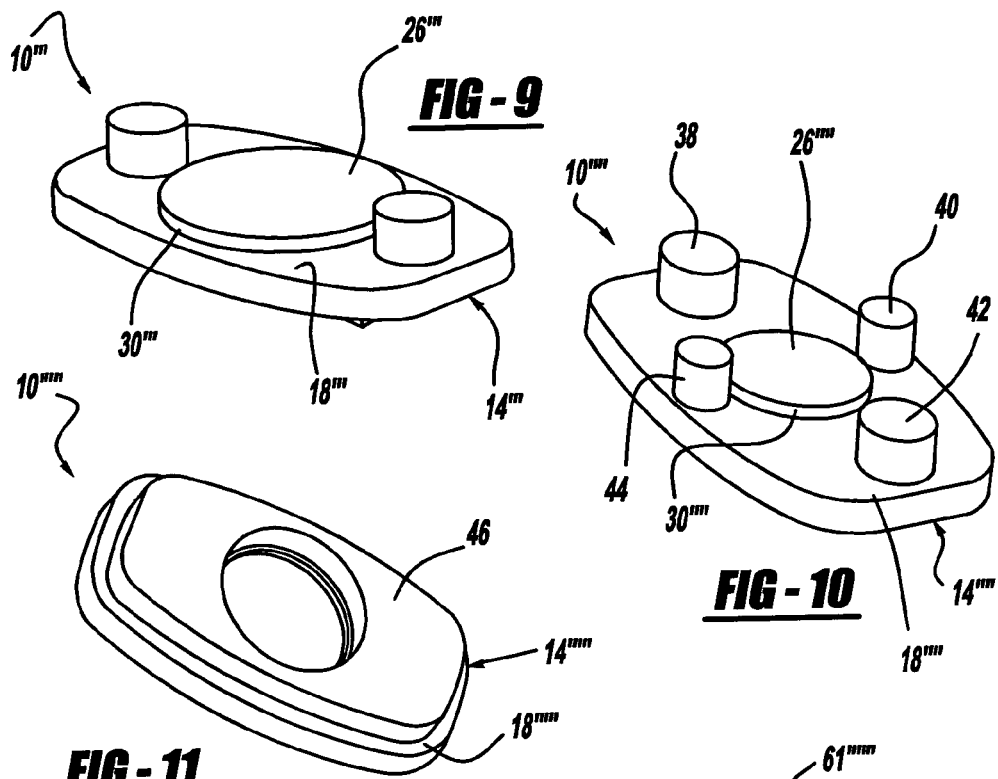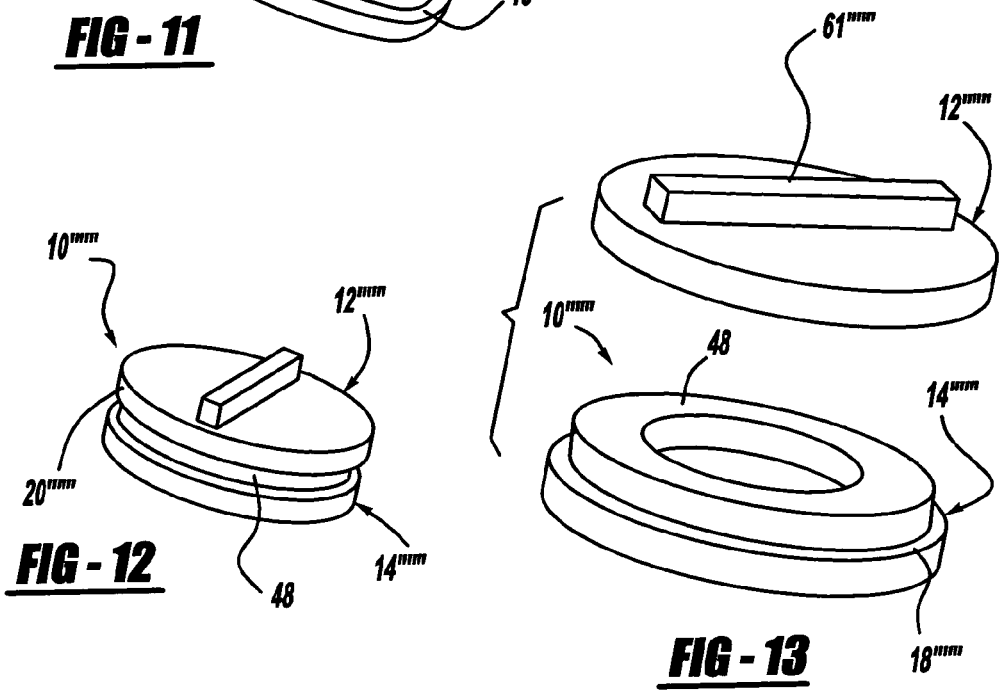

ARTIFICIAL INTERVERTEBRAL DISC

BACKGROUND OF THE INVENTION

1. Technical Field

The present invention relates generally to a spinal implant assembly for implantation into the intervertebral space between adjacent vertebral bones to provide stabilization and continued postoperative flexibility and proper anatomical motion. More specifically, the present invention relates to an artificial intervertebral disc, sometimes referred to as an intervertebral spacer device, for functioning as a load sharing and bearing device for replacement of the damaged, decayed, or otherwise nonfunctioning intervertebral disc.

2. Background of the Invention

The spine is a complex structure consisting of multiple flexible levels. Each level consists of a system of joints defined by adjacent vertebral bones. The system of joints includes intervertebral discs, which are a two-part structure. The disc consists of a nucleus and an annulus. The system allows motion while the facet joints add posterior stabilization to the spinal column. The disc allows motion and cushioning to the joint.

The complex system of the joint is subjected to varying loads and problems over time, including disc degeneration due to a variety of reasons. Disc degeneration can be attributed to aging, damage due to excessive loading, trauma, and other anatomical issues. Facet joints of the structure can be compromised due to the same reasons, as well as due to arthritic changes. Severe joint degeneration and failure can often cause sufficient pain to require surgical intervention.

The current standard method of treatment for severe pain caused by spine joint problems is fusion at the damaged level of the spine. The treatment, when successful, fuses the damaged section into a single mass of bone. The fusion of the joint eliminates motion of the joint, thereby reducing or eliminating pain at that level. Success rates for pain elimination are very high for this method of treatment. However, since the entire spine works as a system, fusion results in complications.

Elimination of motion at the spine alters the biomechanics of the spine at every other level. If one level is fused, then loads are absorbed by one less disc into a system not designed for such change. Thus, the remaining discs must redistribute loads, each disc absorbing a greater load. In addition, the spine flexes to absorb loads. A fusion alters the means by which the spine flexes, which also increases the loads on the remaining healthy discs. In turn, it is well understood that a complication of fusion is that additional fusions may be required in the future as the other discs deteriorate due to the altered biomechanics of the spine. In other words, short-term pain relief is exchanged for long-term alterations of the spine, which, in turn, usually require further surgery.

There are numerous prior art patents addressing the issue of disc replacement. The U.S. Pat. Nos. 6,443,987 B1 and 6,001,130, both to Bryan, disclose polymer composite structures for cushioning intervertebral loads. The U.S. Pat. No. 5,258,031 to Salib, et al. and U.S. Pat. No. 5,314,477 to Marnay disclose ball and socket type implants addressing the issue of intervertebral mobility. These patents are exemplary of a first approach using an elastomer as a motion and dampening structure and a second approach utilizing a ball and socket joint to create a moving pivot joint. There are many variations on these concepts, which include mechanical springs and more complex structural mechanisms. A significant portion of the prior art addresses the issues of intervertebral motion but do not address anatomical loading considerations.

The current state of prior art artificial intervertebral discs are associated with various problems. For example, a number of implants constructed from polymers are of insufficient strength to work effectively in the higher loading areas, such as the lumbar spine. Such polymers often take compressive sets so that the original height of the implant decreases over time. A surgeon must either compensate for the compression by initially using a larger polymer prosthesis and estimate compression or use the appropriately sized polymer prosthesis and later surgically replace the same once the irreversible compression of the prosthesis is unacceptable.

Implants constructed with ball and socket joints severely restrict or eliminate shock cushioning effect of a normal disc. This implant can provide motion, but biomechanically, the ball and socket joint negatively affects other healthy discs of the spine. The result can be long-term problems at other levels of the spine, as seen with the current treatment of fusion.

Other implants, not discussed above, utilize bearing surfaces usually having polyethylene bearing against metal interfaces. Polyethylene as a bearing surface is problematic in large joint replacement due to the wear properties of the material. Since artificial discs are intended to be implanted over long periods of time, such wear can be highly damaging to surrounding tissue and bone.

In view of the above, it is desirable to provide a solution to intervertebral disc replacement that restores motion to the damaged natural disc area while allowing for motion as well as cushioning and dampening, similar to the naturally occurring disc. In addition, it is preferable to allow such motion, cushioning, and dampening while preventing a polymer or elastomeric material from experiencing the relatively high compressive loads seen in the spine. It is also preferable to allow a bearing surface to share the spinal loads with the polymer and elastomeric material. Finally, it is preferable to control changes to the artificial motion intraoperatively to adjust for anatomical conditions.

SUMMARY OF THE INVENTION

In accordance with the present invention, there is provided an artificial intervertebral disc including housing members having spaced inner surfaces facing each other and oppositely facing outer surfaces for engaging spaced apart vertebral surfaces. Bearing surfaces extend from each of the inner surfaces for engaging each other while allowing for low friction and compression resistant movement of the housing members relative to each other while under compression. Load sharing pads disposed between the inner surfaces and about at least a portion of the bearing surfaces share absorption of compressive loads with the bearing surfaces while controllably limiting the relative movement of the housing members.

The present invention further provides a method of assembling an artificial intervertebral disc in vivo by inserting upper and lower housing members into an intervertebral space and disposing cushioning pads between the inner surfaces of the housing members, placing the pads in compression. A pair of disc members are inserted between the inner surfaces of the plates, the disc members having abutting low friction surfaces therebetween. The disc members effectively are surrounded by the pads whereby the disc members and pads are under compressive forces.

Additionally, a method of separating opposing vertebrae at an intervertebral space includes the steps of engaging artificial bearing surfaces between the intervertebral spaces while allowing low friction and compression resistant movement of the bearing surfaces relative to each other, sharing absorption of the compressive forces with at least one load bearing pad disposed about at least a portion of the bearing surfaces, and limiting the relative movement of the bearing surfaces.

DESCRIPTION OF DRAWINGS

Other advantages of the present invention can be readily appreciated as the same becomes better understood by reference to the following detailed description when considered in connection with the accompanying drawings wherein:

FIG. 6 is a top perspective view of an upper housing member made in accordance with the present invention;

FIG. 7 is a top plan view of a lower housing member made in accordance with the present invention;

FIG. 8 is a side perspective view of a third embodiment of the present invention;

FIG. 9 is a perspective view of the present invention with the top housing member removed;

FIG. 10 is a perspective view of an alternative pad configuration of the present invention;

FIG. 11 is a perspective view of a further alternative embodiment of the pad member;

FIG. 12 is a further alternative embodiment of the present invention;

FIG. 13 is an exploded side perspective view of the embodiment shown in FIG. 12;

DETAILED DESCRIPTION OF THE INVENTION

Figure 1:
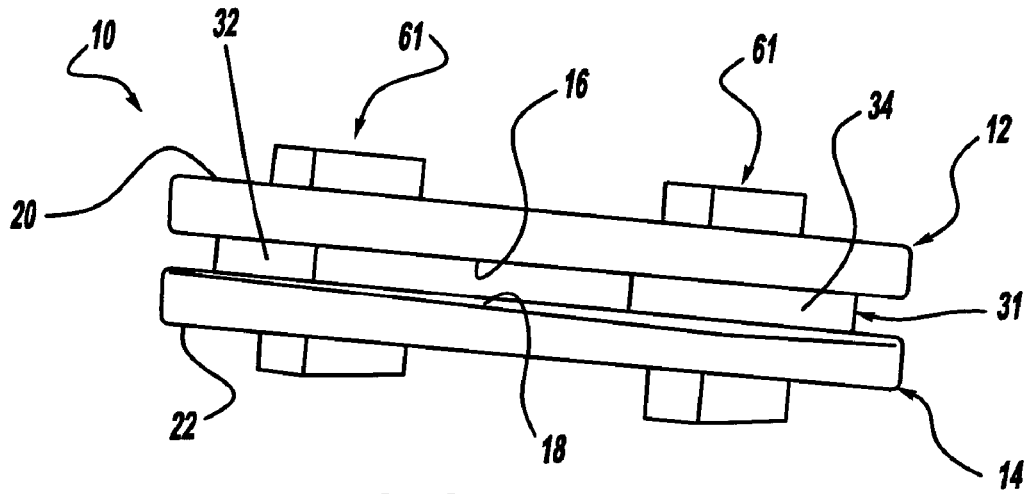
FIG. 1 is a side perspective view of a preferred embodiment of the present invention.

An artificial intervertebral disc constructed in accordance with the present invention is generally shown at 10 in the figures. Like structures of various embodiments are indicated by primed numerals in the Figures. The invention is an artificial intervertebral disc, sometimes referred to by other terminology in the prior art such as intervertebral spacer device, or spinal disc for replacement of a damaged disc in the spine. The invention restores motion to the damaged natural disc that allows for motion as well as cushioning and dampening. As described below in more detail, the present invention also allows changes to the artificial disc motion intraoperatively to adjust for specific anatomical conditions.

Referring to the Figures, the disc 10 includes an upper housing member generally shown at 12 and a lower housing member generally shown at 14. The housing members 12, 14 include spaced inner surfaces 16 and 18 facing; each other and oppositely facing outer surfaces 20, 22 for engaging spaced apart vertebral surfaces. A pair of bearing surfaces 24, 26 extend from each of the inner surfaces 16, 18 for engaging each other while allowing for low friction and compression resistant movement of the housing members 12, 14 relative to each other while under compression. As shown in the various Figures, the bearing surfaces are integral with disc members 28, 30. Alternatively, the bearing surfaces 24, 26 can be surfaces on projections that are integral with and extend from the housing members 12, 14, per se. The housing members 12, 14 can be made from various materials including metals, such as titanium, as well as ceramics, and plastics. If integral with the bearing surfaces 24, 26, the housing members 12, 14 can be made from the preferred material for the bearing discs 28, 30 as discussed above. Based on this teaching, various other configurations can be made by those skilled in the art incorporating the present invention.

The upper and lower bearing surfaces 24, 26 engage each other when disposed correctly opposite each other. The configuration creates a three-dimensional bearing surface. As discussed below, the bearing surfaces 24, 26 are disposed on noncompressible discs or the like, thereby providing structure for absorbing compressive loads placed on the outer surfaces 20, 22 of the housing members 12, 14.

Figure 2:
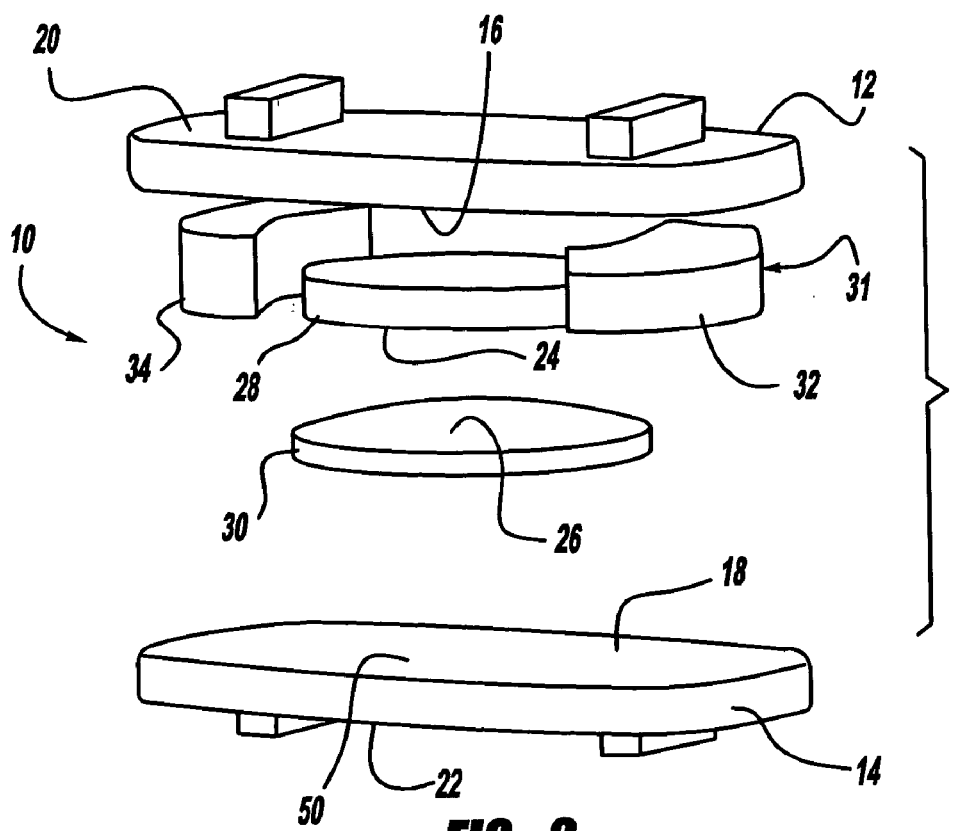
FIG. 2 is a side exploded view of the embodiment shown inn FIG. 1.

Load sharing pads generally shown at 31 and specifically indicated as pads 32 and 34 in FIGS. 1 and 2 are disposed between the inner surfaces 16, 18 and about at least a portion of the bearing surfaces 24, 26 for sharing absorption of compressive loads with the bearing surfaces 24, 26 while limiting relative movement of the housing members 12, 14. More specifically, under in vivo loading conditions, the centralized bearing surfaces 24, 26 not only provide for three-dimensional movement relatively between the housing members 12, 14, but also share with the load sharing pads 32, 34 the function of distributing compressive loads on the device 10 to provide a system for motion and effective load distribution. The centralized low friction and compression resistant bearing surfaces 24, 26 allow full motion in multiple planes of the spine while the load distributing damper and cushioning pads 32, 34 simultaneously share the load. Critical is the function of the pads 32, 34 sharing the load with the bearing surfaces 24, 26. Although the pads 32, 34 can be compressible, the compression is limited by the noncompressibility of the bearing surfaces 24, 26. Likewise, although the bearing surfaces allow for motion in multiple planes, the pads 32, 34 are fixedly secured to the housing members 12, 14, thereby allowing for a degree of flexibility and therefore movement of the housing members 12, 14 relative to each other, yet limiting such movement. In total, each element, the bearing surfaces 24, 26, and pads 32, 34, allow for movement, yet limit such movement, whether it is the sliding movement of the bearing surfaces 24, 26 or the cushioning movement allowed by the pads 32, 34. Each element allows for relative movement, yet each element limits the movement of the other element of the system.

In view of the above, the system allows restoration of normal motion while maintaining load cushioning capabilities of a healthy disc. This is particularly apparent with motion of the spine. Any rotation of the upper and lower housing members 12, 14 causes the load distributing dampening and cushioning pads 32, 34 to absorb some of the load.

As shown in the various figures, the bearing surfaces 24, 26 can include a concave surface portion on one of the upper or lower disc members 28, 30, and a convex surface portion on the other. The concave surface is seated within the convex surface for sliding movement relative thereto effectively resulting in relative pivoting motion of the housing members 12, 14, which compresses at least a portion of the load sharing pads 32, 34 while extending at least a portion of the oppositely disposed load bearing pad 32, 34. Alternatively, either one of the top and bottom disc members 28, 30 can have either of the convex or concave surfaces.

The disc members 28, 30 can be made from a composition that is noncompressible. Such compositions can be selected from the group including ceramics, plastics, and metal bearing materials, such as cobalt and chrome. Alternatively, the housing members 12, 14 can include projections wherein the disc members 28, 30 are effectively integral with the housing members 12, 14. In this situation, the entire housing, including the projections having the bearing surfaces 24, 26 thereon, can be made from the noncompressible material, preferably a ceramic. As stated above, alternative configurations can be made by those skilled in the art once understanding the present invention.

Figure 3:
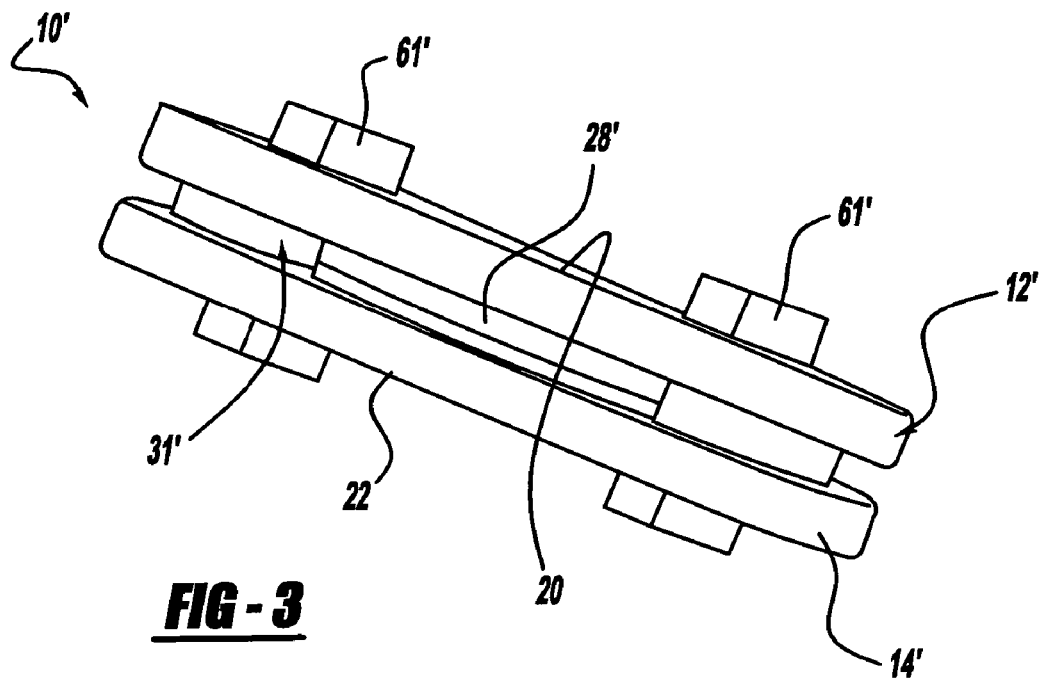
FIG. 3 is a side perspective view of a second embodiment of the present invention.
Figure 4:
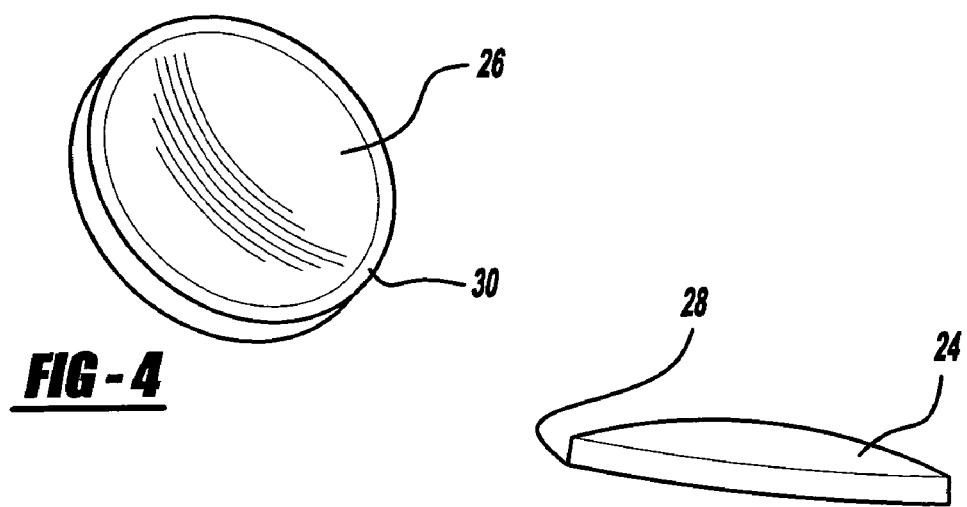
FIG. 4 is a perspective view of a lower disc constructed in accordance with the present invention.
Figure 5:
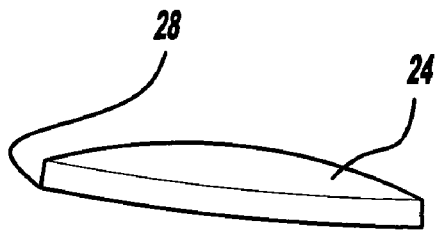
FIG. 5 is a side view of an upper disc constructed in accordance with the present invention.

The load sharing pads 32, 34 can be in various configurations shown in the Figures, such as paired pads 32, 34 shown in FIGS. 1-3. Alternatively, the device 10 can include four oppositely disposed pads 38, 40, 42, 44 as shown in FIG. 10. A further embodiment of the invention is shown in FIG. 11, wherein a single pad 46 substantially covers the surface 18'''' of the housing member 14''''. The pads can contour to the shape of the housing members such as shown in FIGS. 12, 13, wherein the pad member 48 is an annular pad member disposed with a annular housing 12''''', 14'''''. The selection of such housing members 12, 14 and pad members 31 can be determined based on the location of the placement of the device 10 as well as the spacing conditions between the vertebrae and load bearing necessities depending on the level of the spine being addressed. In other words, different shaped devices, such as the round shaped housing members shown in FIG. 12 can be used for placement between smaller discs, such as cervical spines whereas more rectangular shapes, such as the housing members shown in FIGS. 1–11 can be used in between lumbar vertebrae.

The load sharing pads 31, in which ever shape they are configured, are elastic for allowing relative twisting movement between the housing members 12, 14 effecting relative three-dimensional movement between the housing members 12, 14, while limiting the movement and preventing contact between the housing members 12, 14 except for the contact between the bearing surfaces 24, 26. By elastic, it is meant that the pad members 31 are compressible and stretchable, yet provide a self centering effect on the assembly with specific regard to the housing members 12, 14, as well as the bearing surfaces 24, 26. Deflection or rotation of the forces created due to relative movement of the bearing surfaces 24, 26, and likewise the housing members 12, 14, forces the pads 31 to act in such a way to counter the force, thus allowing a unique self-centering capability to the assembly 10. While in an ideal situation, wherein the patient's facets are uncompromised and ligamental balances are intact, this self-centering aspect may not be completely necessary. In other words, the patient's anatomy may still provide stabilization and specifically, ligaments may provide self-centering. However, ligamental imbalance, and damaged facets would normally make an artificial disc questionable, at best, with use of the current technology that is available. In such cases, having the ability to self-center and restrict motion (the pads 31 of the present invention are elastic and thus restrict motion by stretching and returning to rest), the possibility of extending indications to patients currently considered outside of the scope of artificial disc technology will be highly advantageous.

The pads 31 of the present invention provide further advantages to the invention. A key advantage is the ability to adjust the pads 31 to patient and surgeon requirements. In such cases wherein range of motion needs to be restricted due to compromised facets, a harder, less elastic pad can be inserted between the housing members 12, 14. Since this less elastic pad would move and stretch less, the disc would be automatically restricted in motion. This method of adjusting pads can be done intraoperatively to compensate for surgical and patient conditions. To one skilled in the art, one can fine-tune the assembly 10 to a patient's and surgeon's needs with multiple pads of different properties or materials.

The pads 31 are made from a polymer or elastomer that allows deflection under load. Examples of such polymers and elastomers are silicone, polyurethane, and urethane composites. As discussed above with regard to flexibility or elasticity, the content and composition of the pads 31 are adjustable. A highly dense material creates a very rigid disc, while a very soft material creates a very free moving disc. The motion would be restricted in all planes of the pad depending upon these factors. Rotation is also restricted, as well as flexion or movement of the disc. The amount of compression possible is restricted or allowed according to the pads material properties. This is true of motion towards the back or side-to-side motion. Thus, the pads 31 are always in contact and always share the load, under any adjustment of relative positioning of the housing members 12, 14. Since motion forces the pads to be in contact, the pads 31 automatically damper loads imposed by the artificial disc construct 10.

With specific regard to the flexibility or elasticity of the polymer or elastomer composition of the pads 31, the pads can be selected from a composition having a durometer from 20 to 98 on the Shore OO Scale. Alternatively, the pads 31 can be selected from a composition having a durometer from 10 to 100 on the Shore A Scale. A further alternative is for the pads 31 to be selected from a composition having a durometer from 22 to 75 on the Shore D Scale. In any event, the pad members 31 can be selected during the operation and procedure by the clinician to suit a specific situation. Although the pad members 31 can be pre-inserted between the housing members 12, 14 prior to insertion of the device 10 in situ, the various configurations of the present invention can allow for in situ replacement of the pad members 31 so as to custom select the flexibility or elasticity of the members. In this manner, the pad members 31 are custom designed for the individual environment of the intervertebral space into which the device is being disposed.

The disc members 28 and 30, and pads 31 can be contained or locked in position in between the housing members 12, 14 by various means. The disc 28, 30 can be locked to the housing members 12, 14 by a press fit taper, retaining ring, or other means. The key aspect of such locking mechanisms is to prevent the disc members 28, 30 from moving against the upper or lower housing members 12, 14 once installed in order to prevent additional wear.

FIGS. 1 and 2 show disc members 28, 30 disposed in recesses (only the lower recess 50 is shown in FIG. 2 in an exploded view) in each of the inner surfaces 16, 18 of the housing members 12, 14. FIGS. 6 and 7 show plan views of a second embodiment of the housing member 12', 14', wherein each recess 50', 52 includes a ramped surface 54, 56 leading from an outer edge to the inwardly tapered recess portion 50', 52. The ramping 54, 56 allows access of the disc members 28, 30 in between the housing members 12', 14' after placement of the housing members 12', 14' in the intervertebral space. This intraoperative access of the disc members 28, 30 allows the surgeon to test different size disc members under load conditions to perfectly fit the disc members in place. Such an advantage is not obtainable with any prior art device.

Figure 16:
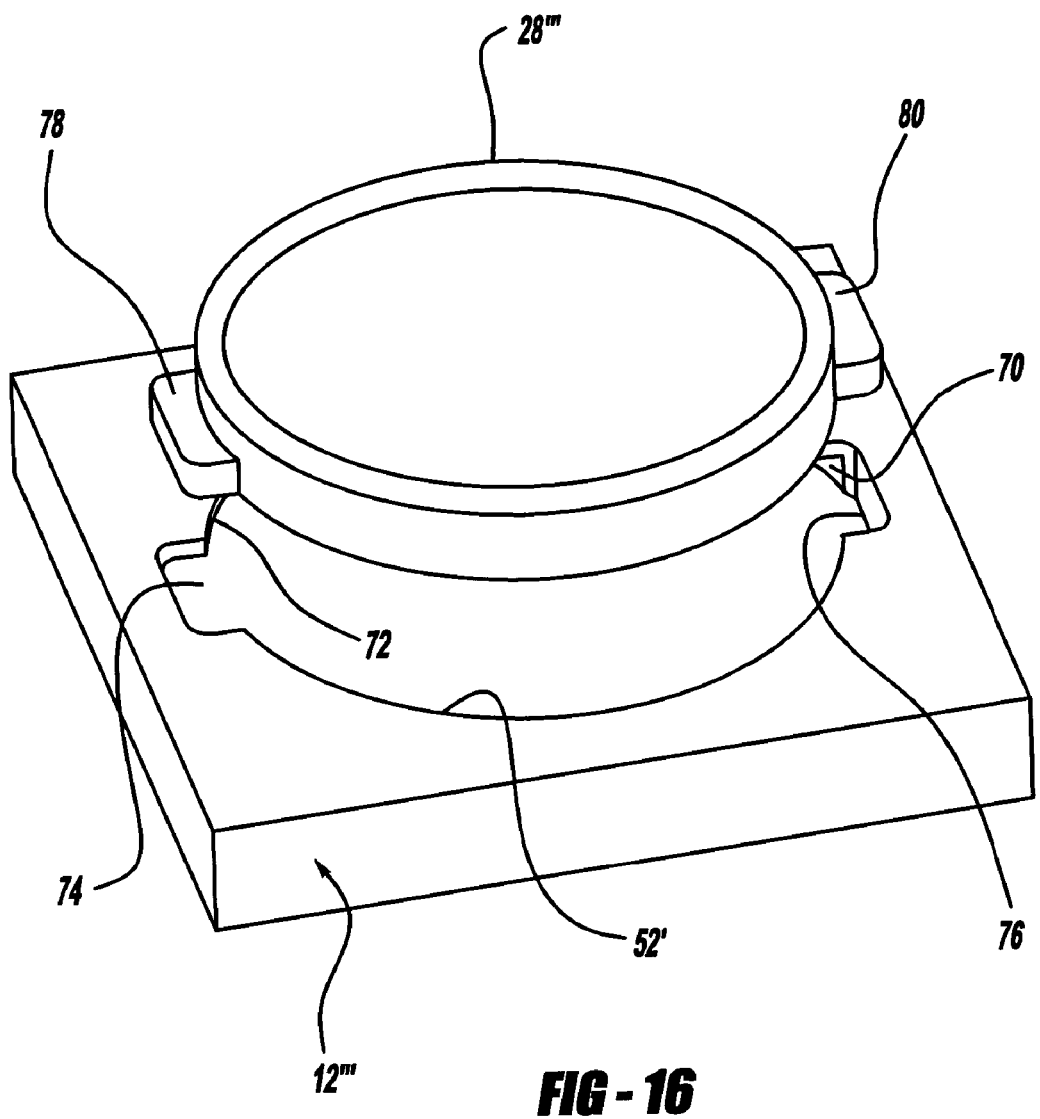
FIG. 16 is an exploded view of a further embodiment of the present invention demonstrating a bayonet type locking of a disc member to a housing member.
Figure 17:
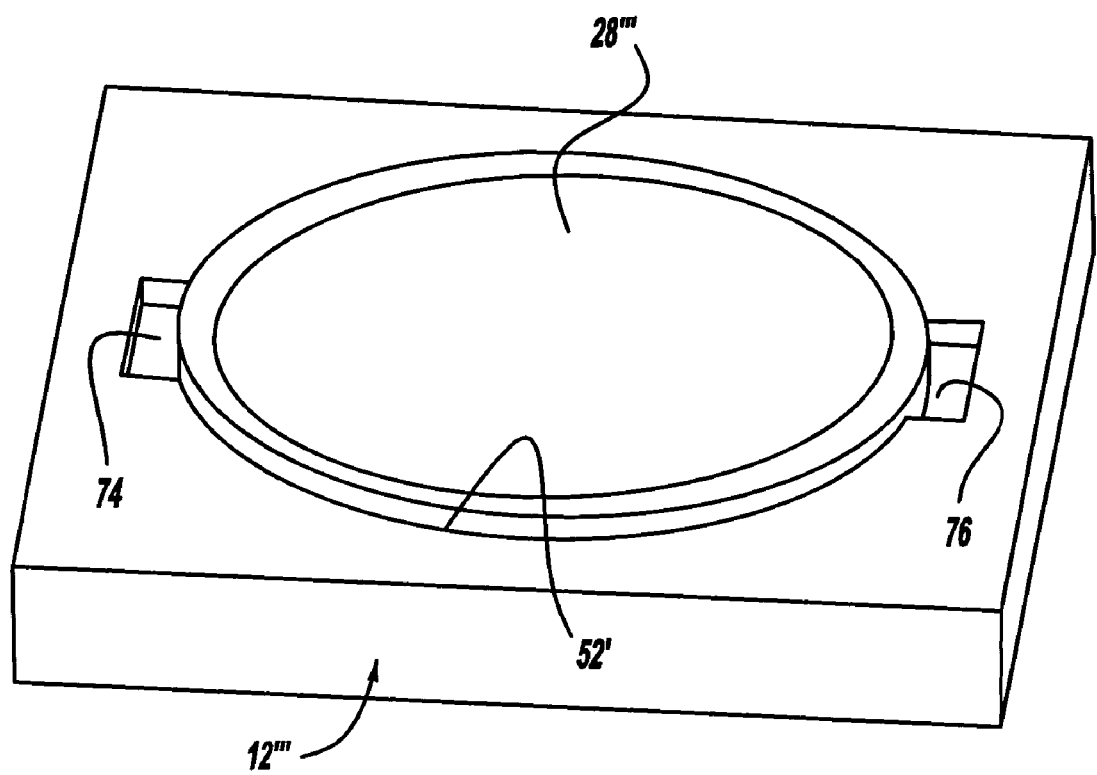
FIG. 17 is a perspective view of the disc member utilizing the bayonet locking mechanism to lock the disc member within a housing member.

An alternative mechanical mechanism for locking the disc members within the housing members are shown in FIG. 16. The representative housing member 12''' includes recess 52'. The recess 52' includes a substantially arcuate peripheral undergroove 70. The groove is defined by a lip portion 72 including at least one and preferably at least two openings 74, 76. The disc member 28''' includes bayonet style flanges 78, 80 extended radially outwardly therefrom, the flanges 78, 80 being shaped so as to be received through recess 74, 76. In operation the disc member 28''' can be disposed within the recess 52' such that the flanges 78, 80 align with recesses 74, 76. Once the disc member 28''' can be rotated thereby providing a bayonet style locking mechanism of the disc member 28''' within the housing 12''', as shown in FIG. 17.

Figure 18:
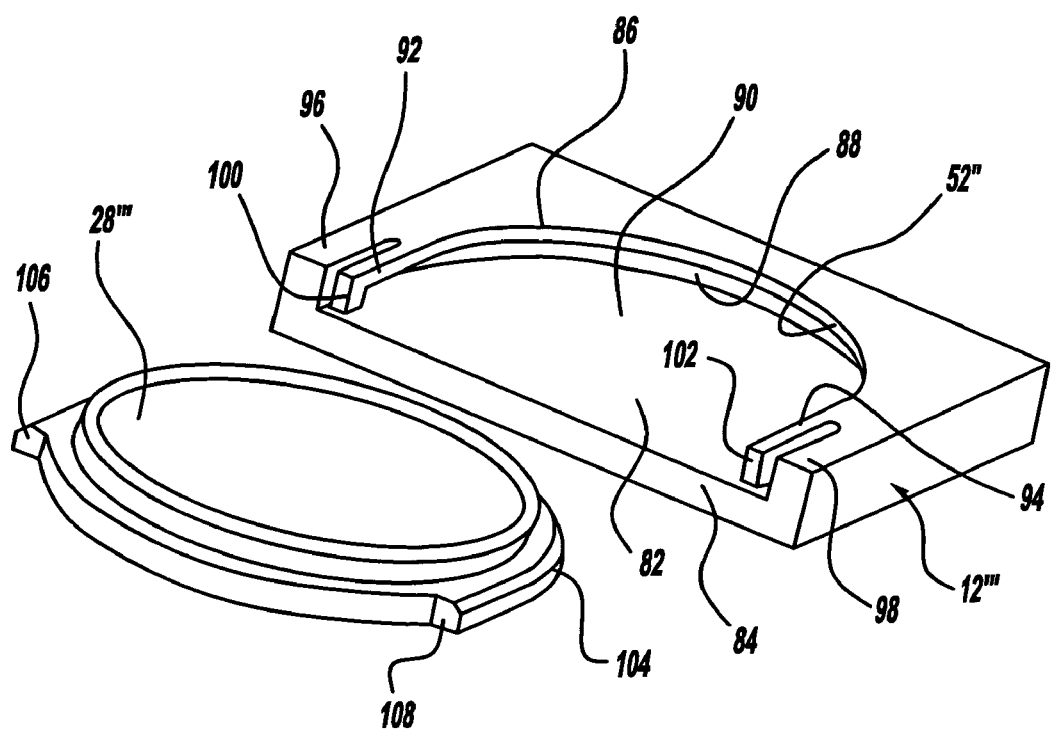
FIG. 18 is an exploded view of a disc member and housing member showing a further embodiment of a locking mechanism for locking the disc member within the housing member.
Figure 19:
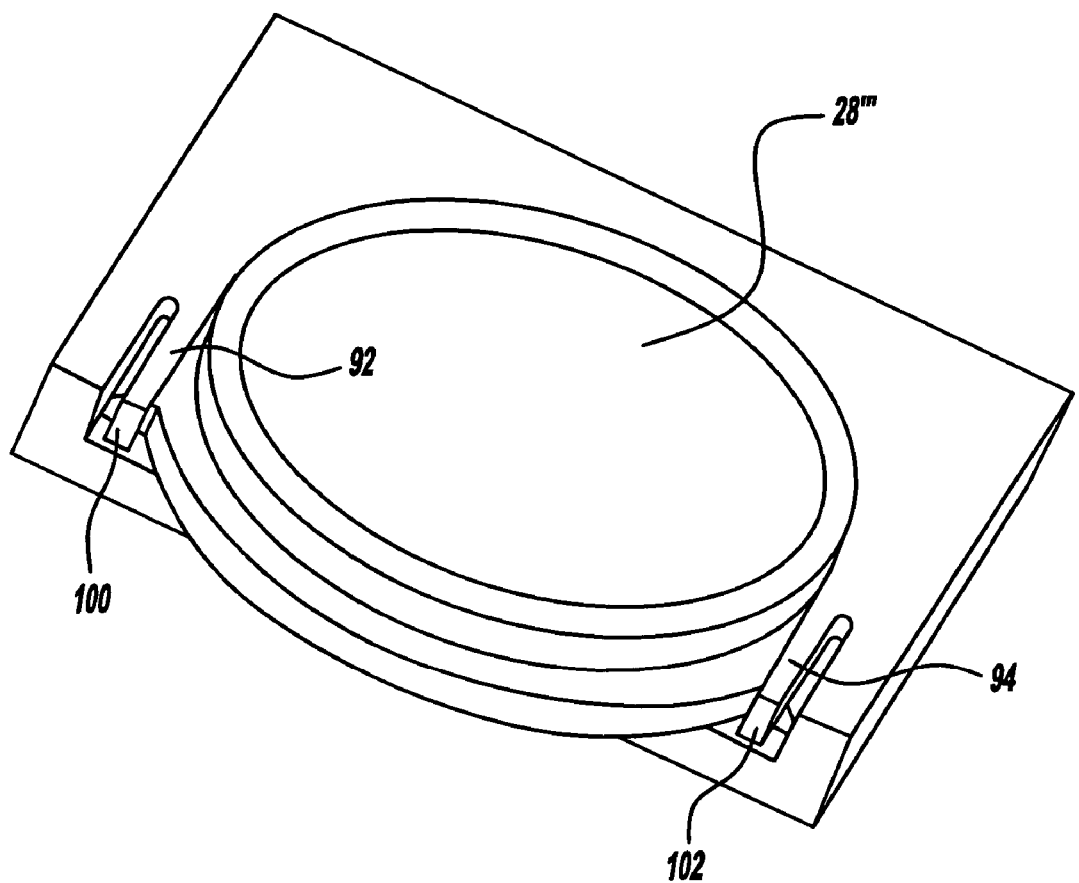
FIG. 19 is a perspective view showing the disc member locked within the housing member.

A further alternative embodiment of the locking mechanism is shown in FIGS. 18 and 19. The housing member 12''' includes a substantially arcuate recess 52'' having an open end portion 82 extending to an edge 84 of the housing member 12'''. The recess 52'' includes a lip portion 86 extending about a substantial portion thereof defining an inner groove 88 between the seating surface 90 of the recess 52'' and the lip portion 86. Arm portions 92, 94 are extensions of the lip portion 86 but extend from and are separate from peripheral ends 96, 98 of the housing member 12'''. The arm portions 92, 94 have a spring-like quality such that they can be deflected outwardly from the arcuate circle defined by the recess 52''. Each of the arms 92, 94 has an elbow portion 100, 102 extending from each arm portion 92, 94 towards the seating surface 90, respectively. The disc member 28''' includes a substantially arcuate peripheral, radially outwardly extending flange portion 104. The flange portion 104 includes two abutment edges 106, 108. In operation, the flange 104 and disc member 28''' are disposed within the annular recess or groove 88, deflecting outwardly the arms 92, 94. Once disposed in the recess 52'', as shown in FIG. 19, the elbows 100, 102 engage the abutment surfaces 106, 108 of the disc member 28''' thereby locking the disc member 28''' in place. Outward deflection of the arms 92, 94 can selectively release the disc member 28''' from locked engagement to provide for further adjustment of the selection of the disc member during an operation procedure.

Also, as best shown in FIGS. 6 and 7, the pads members 31 can be disposed in recesses 58, 60 in the lower and upper housing members 12', 14' respectively. It is preferable to permanently adhere the pad members 31 to the housing members 12', 14' by use of mechanical mechanisms and/or various adhesives, such as cyanoarylates, urethanes, and other medical grade adhesives. This list of adhesives, as with other listings of ingredients in the present application, is merely exemplary and not meant to be exhaustive.

Examples of mechanical mechanisms for locking the pad members 31 into recesses in the housing members are shown in FIGS. 20–23. One such mechanism is an undercut locking mechanism shown in FIGS. 20–22. Housing member 12'''' includes a central recess 52 such as shown in FIG. 6 having a ramp portion 56. The ramp portion 56 includes a centrally located tongue groove 57 allowing for the insertion of a spatula type device under a disc member disposed within the recess 52 for releasing the disc member from the recess, similar to the use of a shoehorn type mechanism. Recesses 60' include undercut recesses 110, 112 for locking engagement with a peripheral flange portion 114 extending from an edge 116 of a pad member 31'. Since the pad member is made from a deflectable material, the flange portion 114 can be force-fit into and seated within the undercut 110, 112. The undercut locking mechanism effectively prevents the pad member 31' from disengagement with the housing member 12'''' in situ. Of course, the upper flange 118 would be locked within a similar undercut locking detail of recesses within the opposing housing member (not shown).

Figure 23:
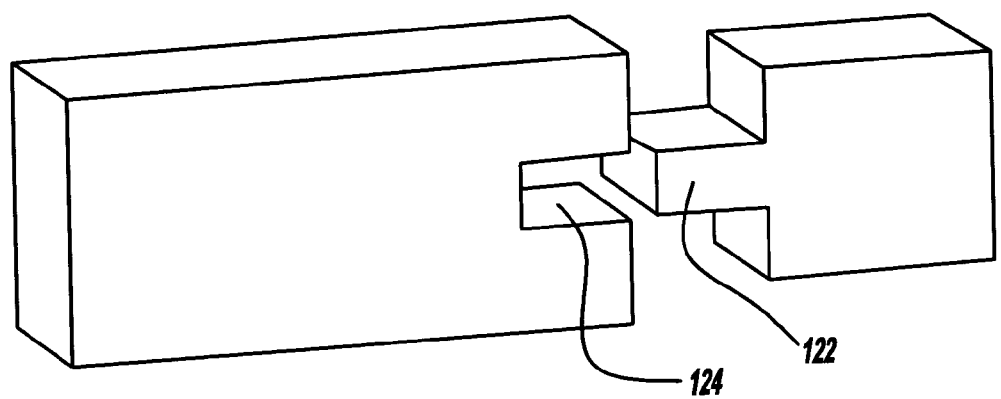
FIG. 23 shows a further embodiment of a locking mechanism made in accordance with the present invention.

An alternative locking mechanism between the pad member and housing member can be a tongue-and-groove relationship as shown in FIG. 23. Either the pad or the housing can include the tongue portion 122 and the other pad and housing members can include the groove 124. In other words, either of the locking members can include the tongue 122 and the other of the members being locked would include the groove 124. An alternative of this or the other locking mechanism shown is that the recess and/or pad can include multiple grooves or slots as well as multiple tongues.

The various recesses or pockets 50', 52, 58, 60 can be of different relative sizes and shapes. For example, the upper housing member 12' may have a larger recess or pocket for seating a relatively larger one of said discs 28 and the lower housing member 14' may be include a smaller (larger and smaller referring to diameter of the annular recess) of the recesses or pockets for seating a relatively smaller one of the lower disc 30, thereby providing for an increased range of motion at the bearing surface interface.

Figure 14:
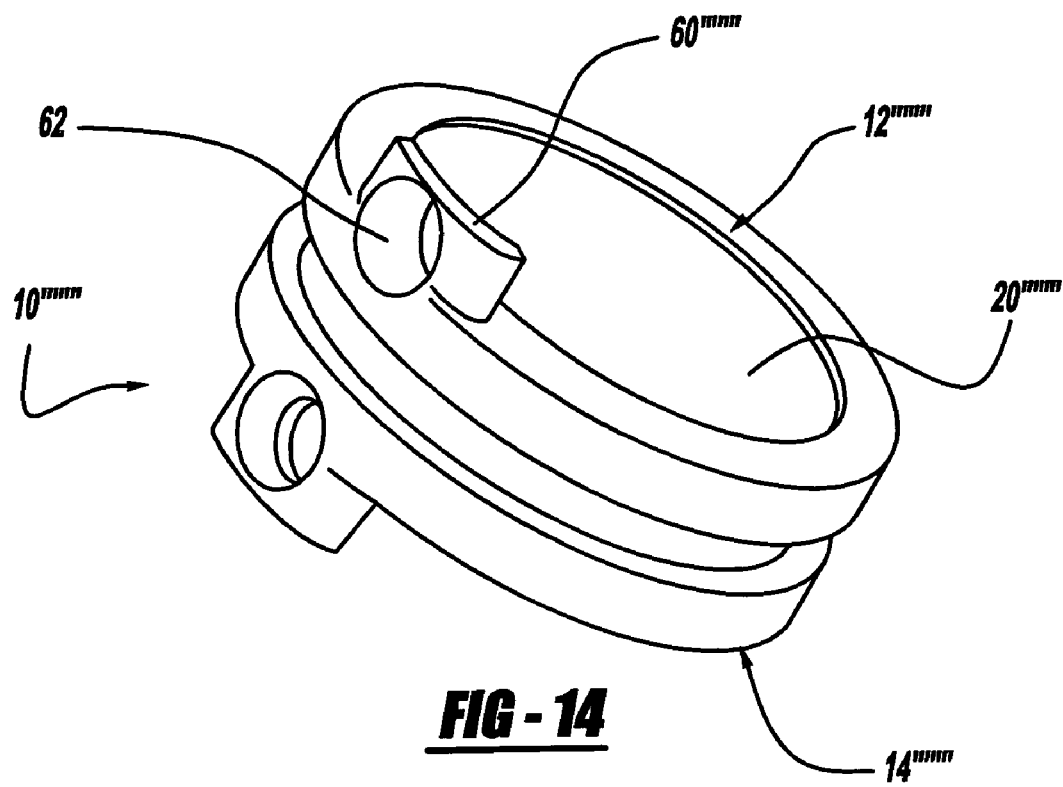
FIG. 14 shows an alternative embodiment of the housing members of the present invention.
Figure 15:
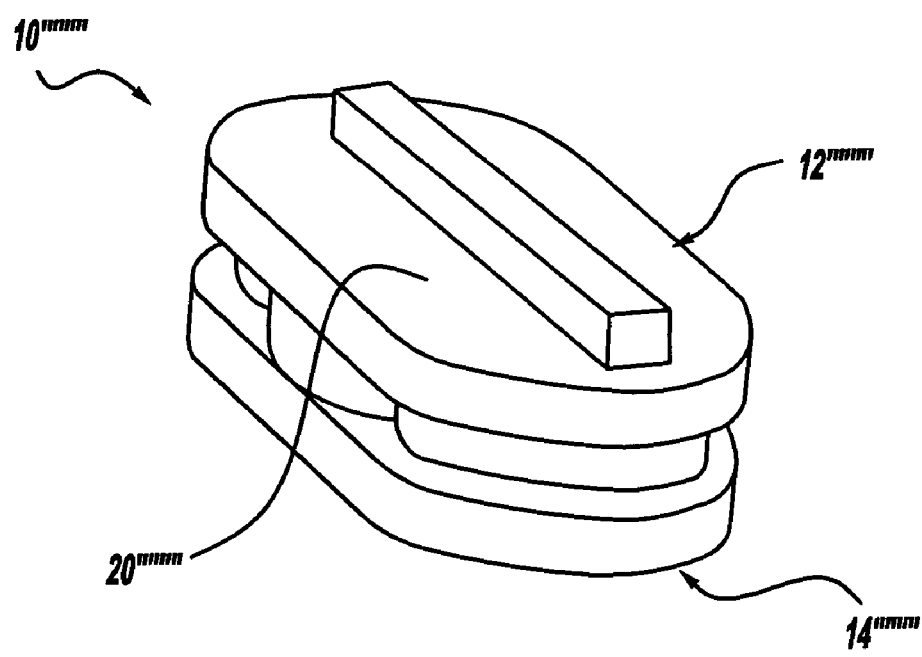
FIG. 15 shows a further alternative embodiment of the housing members of the present invention.

The various Figures show that the outer surfaces 20, 22 of the various embodiments of the housing members 12, 14 can include flanges generally indicated at 60. The flanges 60 or fins, as they are sometimes referred to in the art, provide a mechanism for fixation to the intervertebral surfaces. Various embodiments, such as those shown in FIGS. 1 and 2 are dual fin constructs. Other embodiments, such as those shown in FIGS. 8, 12, and 13 are single fin or single flange constructs. Depending upon the nature of the surfaces to which the outer surfaces 20, 22 are to abut, the surgeon can select various flange or fin configurations. Additionally, the fins 60 can be located in alternative positions, either centrally as shown in many of the Figures, or peripherally, as shown in FIG. 14, for a specific use with anterior extension plates, as with screw fixations. The flanges, such as flange 60''''' can include a bore 62 therethrough, which can be either a smooth surface or threaded depending on its intended use.

The outer surfaces 20, 22 can be smooth, which allows for easier revision as it allows for minimal to no ingrowth or they can be textured. Texturing of the outer surfaces 20, 22 allows ingrowth for long-term fixation of the assembly 10. Porous coatings, plasma spray, grit blasting, machining, chemical etching, or milling are examples of techniques for creating ingrowth capable surfaces. Coatings that enhance bone growth can also be applied. Examples of such coatings are hyroxyapatite and bone morphogenic proteins.

Figure 20:
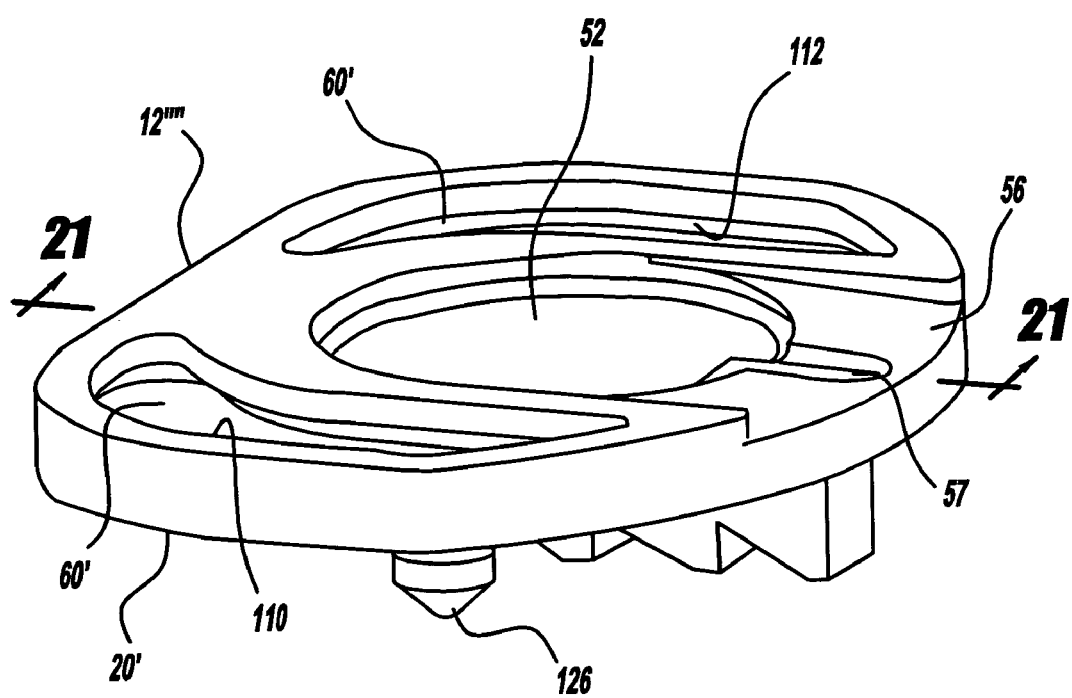
FIG. 20 is a perspective view of the a further embodiment of the housing member.
Figure 21:
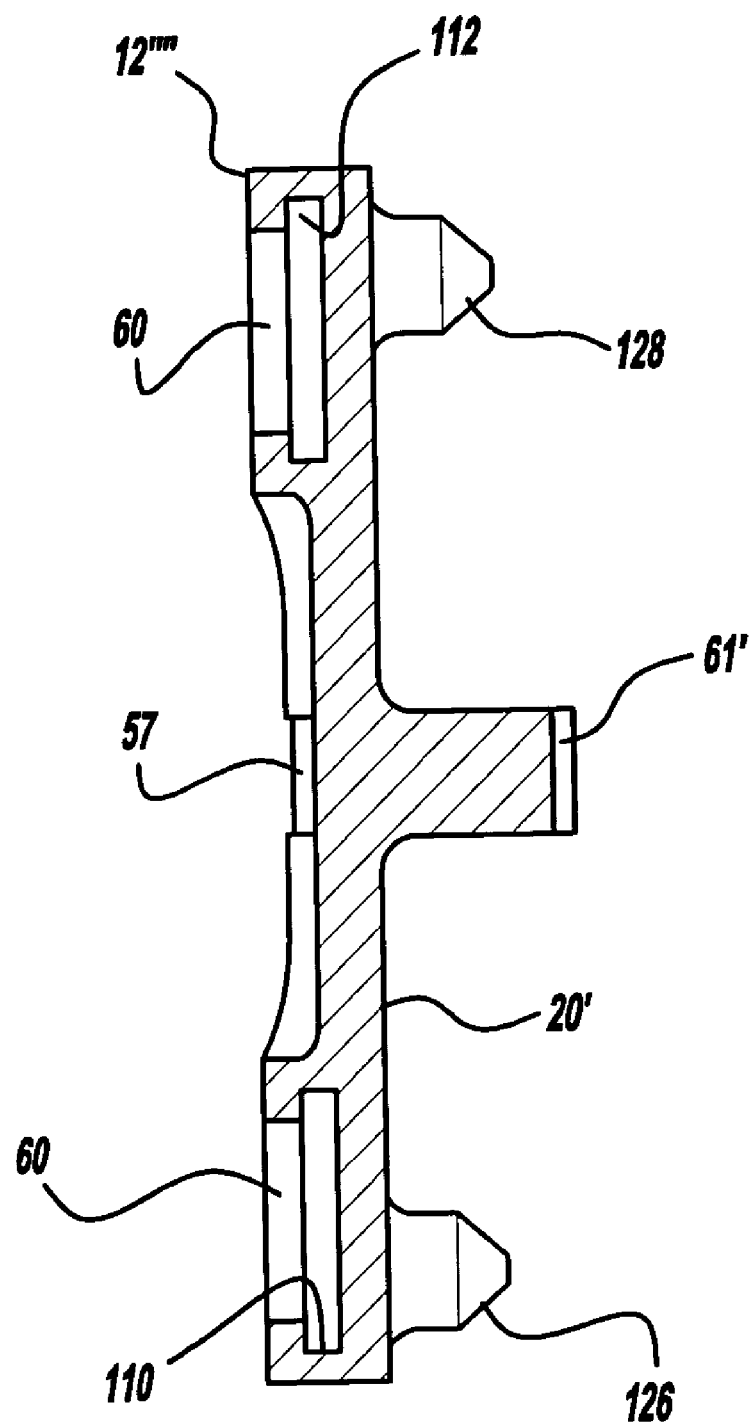
FIG. 21 is a cross sectional view taken along line 21—21 in FIG. 20.
Figure 22:
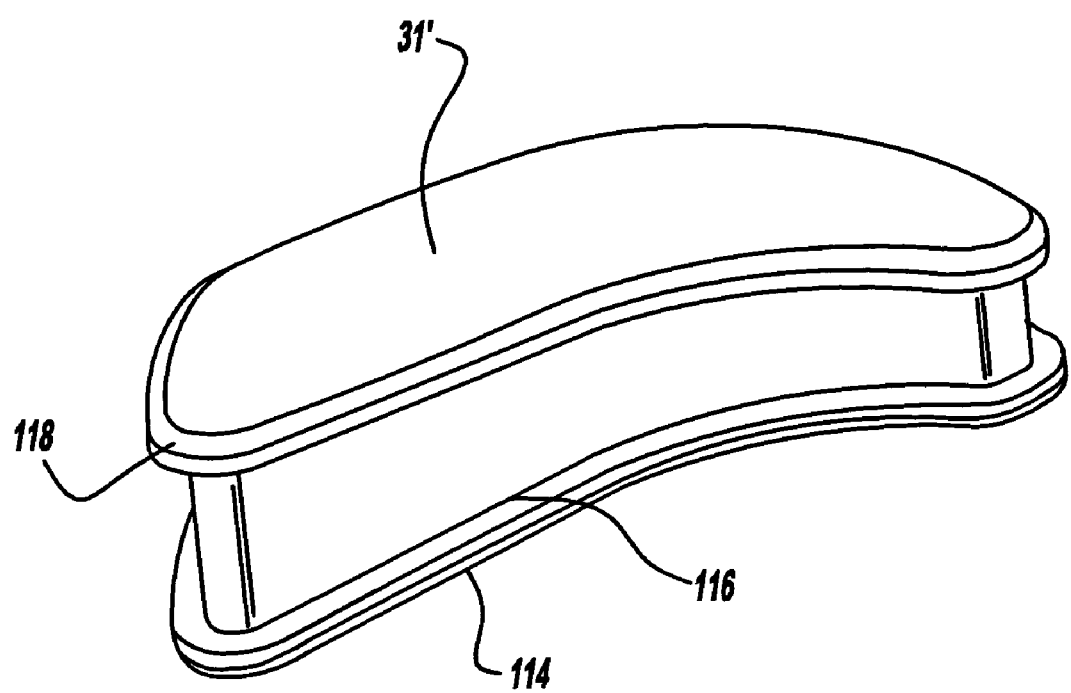
FIG. 22 is a perspective view of a load sharing pad member including flanges for locking engagement in the recesses of the housing member shown in FIGS. 20 and 21.

FIGS. 20 and 21 provide structure for further rotational stability of the device in situ. The housing member 12'''' includes pointed portions 126, 128 extending from the outer surface 20' thereof. The point members 126, 128 function in conjunction with the flange portion 61' to engage an opposing vertebral surface. The point portions 126, 128 being disposed radially peripherally from the centrally disposed flange 61' provide at least a three-point engagement of the vertebral surface thereby preventing rotation of the housing member 12'''' relative thereto. Of course, the point portions 126, 128 can be in made in various configurations and extend various amounts from the outer surface 20' to be custom suited to a specific vertebrae surface shape.

Various methods can be utilized for insertion of the present invention in situ. For example, an assembled device 10 as shown in FIG. 1, can be disposed between the intervertebral spaces during surgery, after calculation of space, depth, and height. Alternatively, opposing housing members 12, 14 can be disposed between the intervertebral spaces and pads 31 and disc members 24, 26 can be tested in situ prior to fixation thereof to allow for custom sizing. Accordingly, the present invention broadly provides a method of assembling an artificial intervertebral disc 10 in vivo by inserting upper and lower housing members 12, 14 into an intervertebral space and disposing cushioning pads 31 between the inner surfaces 16, 18 of the housing members 12, 14, thereby placing the pads in compression. The pair of disc members 28, 30 are inserted between the inner surfaces of the plates 16, 18. The disc members 28, 30 have abutting low friction surfaces 24, 26 therebetween. The disc members 28, 30 are surrounded by the pads 31, whereby the disc members 28, 30 and pads 31 are under compressive forces and share such compressive forces. This step of the bearing surfaces 24, 26 and shock absorbing pads 31 sharing absorption of the compressive forces and limiting the relative movement of the housing members 12, 14 is an advantage not found in the prior art.

What is claimed is:

1. An artificial intervertebral disc comprising:
   housing members including spaced inner surfaces facing each other and oppositely facing outer surfaces for engaging spaced apart intervertebral surfaces;
   bearing means extending from each of said inner surfaces for engaging each other while allowing for low friction and compression resistance relative to each other while under compression;
   load sharing means disposed between said inner surfaces and about at least a portion of said bearing means for sharing absorption of compressive loads with said bearing means while limiting the relative movement of said housing members, said bearing means including a concave surface portion extending from one of said inner surfaces and a convex surface portion extending from the other of said inner surfaces and seated against said concave surface portion for sliding movement relative thereto effectively resulting in relative pivoting motion of said housing members which can compress at least a portion of said load sharing means while distending at least a portion of said load bearing means, the load sharing means being elastic for allowing relative twisting movement between said housing members effecting relative three dimensional movement between said housing members while limiting the movement and preventing contact between the housing members except for the bearing means;
   a pair of disc members, each of said disc members including one of said bearing means, said inner surfaces of said housing members including disc seating means for seating one of said disc members therein in opposing relationship of the other of said disc members seated in said seating means of the other of said housing members, said disc seating means including a pocket recessed into each of said inner surfaces of said housing members; and
   locking means for selectively preventing relative movement of said disc members and said housing members once each disc member is seated in its respective pocket, said locking means for each disc member comprising at least one undercut groove disposed about one of said pocket and said radial periphery of the disc member, and at least one flange disposed about the other of said pocket and said radial periphery of the disc member for locking engagement with said undercut groove.

2. A disc according to claim 1, wherein said locking means includes at least one undercut groove disposed about said pocket and said disc member includes at least one radially outwardly extending flange for locking engagement within said undercut groove.

3. A disc according to claim 2 wherein said flange includes at least one radially outwardly extending bayonet portion.

4. A disc according to clam 1 wherein said locking means includes at least one undercut groove disposed about a radial periphery of said disc member and said pocket of said housing member includes at least one radially inwardly extending flange for locking engagement within said undercut groove.

5. A disc according to claim 1, including a ramped surface extending from an edge of said inner surface of at least one of said housing members to said pocket allowing for lateral insertion of said disc members into said pockets when said housing members are disposed in spaced relationship to each other in an intervertebral space.

6. A disc according to claim 1 further defined as said housing members being an upper member and a lower member for relative positioning between vertebrae, said upper member including a relatively larger one of said pockets for seating a relatively larger one of said disc members having a concave surface and said lower member including a relatively smaller pocket for seating a relatively smaller one of said discs thereby providing an increased range of motion at the bearing surface interface.

7. A disc according to claim 1, wherein said disc members are made from a composition selected from the group including ceramics, plastics, and metal bearing materials.

8. An artificial intervertebral disc comprising:
   housing members including spaced inner surfaces facing each other and oppositely facing outer surfaces for engaging spaced apart intervertebral surfaces;
   bearing means extending from each of said inner surfaces for engaging each other while allowing for low friction and compression resistance relative to each other while under compression;

load sharing means disposed between said inner surfaces and about at least a portion of said bearing means for sharing absorption of compressive loads with said bearing means while limiting the relative movement of said housing members, said bearing means including a concave surface portion extending from one of said inner surfaces and a convex surface portion extending from the other of said inner surfaces and seated against said concave surface portion for sliding movement relative thereto effectively resulting in relative pivoting motion of said housing members which can compress at least a portion of said load sharing means while distending at least a portion of said load bearing means, the load sharing means being elastic for allowing relative twisting movement between said housing members effecting relative three dimensional movement between said housing members while limiting the movement and preventing contact between the housing members except for the bearing means;

a pair of disc members, each of said disc members including one of said bearing means, said inner surfaces of said housing members including disc seating means for seating one of said disc members therein in opposing relationship of the other of said disc members seated in said seating means of the other of said housing members, said seating means including a pocket recessed into each of said inner surfaces of said housing members; and locking means for selectively preventing relative movement of said disc member and said housing member once said disc member is seated in said pocket, wherein said locking means includes a retaining ring operatively connected to said pocket.

9. An artificial intervertebral disc comprising:

housing members including spaced inner surfaces facing each other and oppositely facing outer surfaces for engaging spaced apart intervertebral surfaces;

bearing means extending from each of said inner surfaces for engaging each other while allowing for low friction and compression resistance relative to each other while under compression; and load sharing means disposed between said inner surfaces and about at least a portion of said bearing means for sharing absorption of compressive loads with said bearing means while limiting the relative movement of said housing members, the load sharing means including at least one pad member disposed and retained between said inner surfaces of said housing members and having cushioning and elastic properties for countering and thereby self centering against forces caused by relative movement of said housing member while compressive forces are applied to said outer surfaces of said housing members, the housing members including seating means for seating the pad members between the inner surfaces, the seating means including at least one pocket recessed into the inner surface of the housing member for seating a portion of the pad member therein, the pocket including at least one undercut recess about at least a portion thereof and said pad members including at least one outwardly extending flange portion for being seated within said recess to lock said pad members in a desired position relative to said housing member.

10. An artificial intervertebral disc comprising:

housing members including spaced inner surfaces facing each other and oppositely facing outer surfaces for engaging spaced apart intervertebral surfaces;

bearing means extending from each of said inner surfaces for engaging each other while allowing for low friction and compression resistance relative to each other while under compression; and load sharing means disposed between said inner surfaces and about at least a portion of said bearing means for sharing absorption of compressive loads with said bearing means while limiting the relative movement of said housing members, the load sharing means including at least one pad member disposed and retained between said inner surfaces of said housing members and having cushioning and elastic properties for countering and thereby self centering against forces caused by relative movement of said housing member while compressive forces are applied to said outer surfaces of said housing members, the housing members including seating means for seating the pad members between the inner surfaces, the seating means including at least one pocket recessed into the inner surface of the housing member for seating a portion of the pad member therein, the pad member including at least one peripherally located recess about an edge portion thereof and said pocket including at least one inwardly extending flange portion including at least one inwardly extending flange portion for being seated within said recess to lock said pad member in a desired position relative to said housing member.

* * * * *